United States Patent [19]
Koranda et al.

[11] Patent Number: 5,603,712
[45] Date of Patent: Feb. 18, 1997

[54] BIPOLA SUCTION TONSILLAR DISSECTOR

[75] Inventors: Frank C. Koranda, 4341 Homestead Cir., Prairie Village, Kans. 66208; Charles L. Poynter, Kansas City, Mo.

[73] Assignee: Frank C. Koranda

[21] Appl. No.: 464,289

[22] Filed: Jun. 5, 1995

[51] Int. Cl.⁶ .................................................. A61B 17/39
[52] U.S. Cl. ................................. 606/51; 606/52; 604/35
[58] Field of Search ................................. 606/48, 50–52; 604/35

[56] References Cited

U.S. PATENT DOCUMENTS

| | | | |
|---|---|---|---|
| 4,567,890 | 2/1986 | Ohta et al. | 606/51 |
| 4,651,734 | 3/1987 | Doss et al. | |
| 5,122,139 | 6/1992 | Sutter. | |
| 5,151,102 | 9/1992 | Kamiyama et al. | |
| 5,197,964 | 3/1993 | Parins. | |
| 5,217,458 | 6/1993 | Parins. | |
| 5,258,006 | 11/1993 | Rydell et al. | |
| 5,267,998 | 12/1993 | Hagen. | |
| 5,269,780 | 12/1993 | Roos. | |
| 5,269,782 | 12/1993 | Sutter. | |
| 5,281,216 | 1/1994 | Klicek. | |
| 5,290,284 | 3/1994 | Adair. | |
| 5,290,285 | 3/1994 | Kirwan, Jr. | |
| 5,290,286 | 3/1994 | Parins. | |
| 5,464,405 | 11/1995 | Fujitsu et al. | 606/51 |

OTHER PUBLICATIONS

Microsurgical Bipolar Cautery Tonsillectomy by Marie Andrea, M.D. Laryngoscope, vol. 103, No. 10, Oct. 1993.
Electrodissection Tonsillectomy by Thomas A. Weimert, M.D. et al, Arch Otolaryngol Head Neck Surg–vol. 116, Feb. 1990, pp. 186–188.
Diathermy haemostasis at tonsillectomy: Current practice—A Survey of U.K. otolaryngologists by G. E. Murty F.R.C.S. et al, Journal of Laryngology and Otology, 1990, vol. 104, pp. 549–552.
Is Outpatient Suction Cautery Tonsillectomy Safe in a Community Hospital Setting? by Rex S. Haberman II, M.D. et al., Laryngoscope 100: May 1990, pp. 511–515.
Spec sheet for Codman Bipolar Forcep Coagulators.
Brochure for Smith & Nephew Richards Non–Stick Bipolar Forceps for Cooler, Cleaner, Faster Hemostasis.
Catalog for Storz Surgical Instruments.

*Primary Examiner*—Lee S. Cohen
*Attorney, Agent, or Firm*—Hovey, Williams, Timmons & Collins

[57] ABSTRACT

A bipolar suction tonsillar dissector is provided which is especially useful in tonsillectomies and adenotonsillectomies to minimize hemorrhage and tissue damage by promoting surgical efficiencies. The instrument hereof includes a pair of arms connected by a connector plug to define a forceps. One arm includes a tubular suction channel which may be connected to a source of vacuum and presents an opening at the remote end through which undesired or excess fluid may be removed from the dissection site. The other arm includes a dissecting blade for enabling the surgeon to remove or cut away tissue. Advantageously, the blade and structure adjacent the opening define electrodes whereby the surgeon may, without delay in switching instruments, electrocoagulate hemorrhaging blood vessels and then return to dissection and suction of the blood or other fluid.

13 Claims, 1 Drawing Sheet

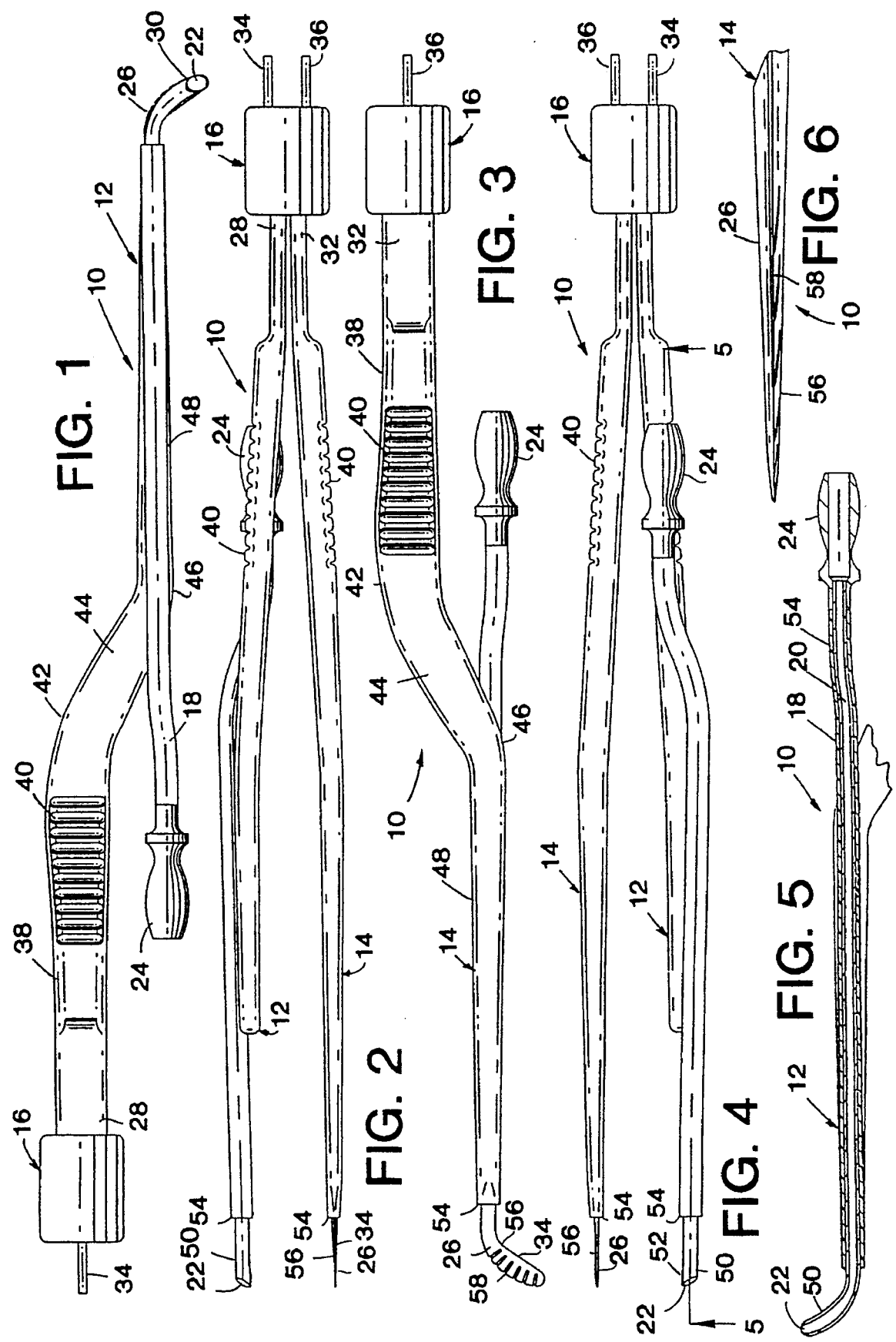

BIPOLA SUCTION TONSILLAR DISSECTOR

BACKGROUND OF THE INVENTION

1. Field of the Invention

This invention relates to a surgical instrument particularly useful in tonsillar surgeries which greatly facilitates the surgeon's task of dissecting tissue and avoiding excessive bleeding. In particular, this invention relates to a dissector whereby the surgeon can use suction to remove excess fluid and bipolar electrocoagulation without the necessity of changing instruments.

2. Description of the Prior Art

The performance of tonsillectomy and adenotonsillectomy surgical procedures are common throughout the United States and elsewhere, with an estimated 340,000 performed in the United States each year. The major complication of tonsillectomy is post-operative hemorrhage. As the techniques by which tonsils are removed over time have been refined, electrocoagulation has been used more frequently to achieve hemostasis.

Suction electrocoagulation for removal of tonsils is an effective method with minimal blood loss. Blood vessels are electrocoagulated as they are encountered. However, with ordinary coagulation, the trauma to tissues may extend 1 to 2 mm beyond the point of contact. This causes greater tissue necrosis and may lead to late post-operative bleeding. However, suction electrocoagulation devices heretofore presented are not good dissecting instruments. Nonetheless, there is a tendency to use such electrocoagulation devices to cut through adherent tissue which leads to even greater tissue trauma. The other option is to switch back and forth between using a suction electrocoagulation device and a dissecting instrument such as the Fischer "hockey-stick" style dissector. Such switching between instruments prolongs the surgery and the time the patient must remain under anesthetic, permits additional hemorrhaging during instrument changes, and decreases efficiency.

Another method for the removal of tonsils is with a bipolar electrocoagulating forceps. With bipolar electrocoagulation, tissue damage is limited to the tissue between the tines of the bipolar coagulator. A recent study by Dr. Mario Andrea in the October, 1993 edition of *Laryngoscope* used this technique in 265 patients. The study demonstrated its effectiveness and also negligible delayed post-operative bleeding. The bipolar electrocoagulating forceps is designed principally for coagulation. If suction is needed, which is not uncommon, another instrument must be introduced into the operating field. To some degree, a bipolar coagulator may be used as a dissecting instrument; there are many instances where conventional dissection is more advantageous as dissection is not inherent in the bipolar coagulator's design.

Thus, there has developed a need for a surgical instrument which enables the surgeon to take advantage of the optimum features of dissection, bipolar electrocoagulation, and suction and thereby remove the temptation to make one instrument "do" for another. The techniques of tonsillectomy with the suction electrocoagulation device or with the bipolar electrocoagulation forceps were both developed for a more efficient method with less operative and delayed post-operative bleeding. However, there are drawbacks to both techniques which may be obviated if the functions of bipolar electrocoagulation, suction, and dissection could be combined into one instrument.

SUMMARY OF THE INVENTION

The goal of increased efficiency, reduced hemorrhage, and optimum technique has been achieved by the development and employment of the bipolar suction tonsillar dissector of the present invention. That is to say, the present invention produces greater efficiency in the operating field by the economy of motion in using a single instrument in the surgeon's hands which obviates the need to switch back and forth between different instruments.

The bipolar suction tonsillar dissector of the present invention broadly includes a pair of arms which are joined by a connecting plug into a forceps orientation. The opposed arms are substantially parallel and biased into a separated but parallel position whereby the remote ends of the arms can be closed and then spring back to a separated position. One of the arms is provided with a tubular suction channel which communicates between an opening at the remote end and a relatively proximate connection or fitting for fluidic coupling to a source of vacuum. The other arm is provided with a dissecting blade at the remote end thereof. The remote ends of the arms provide relative poles for the passage of electrical current therethrough when joined, or more appropriately when tissue is clasped therebetween for bipolar coagulation.

In its most preferred embodiment, the remote ends are oriented at obtuse angles to shank portions of the arms, thereby providing a bayonet forceps. The remote ends are angled about 120° relative to the shank, thereby extending away from the holder and providing a good cutting edge and good extension of the opening for suction. The opening is positioned on a tine of the second arm and angled to make precise contact with the "hockey stick" blade on the second arm for the purpose of bipolar coagulation. Except for the tines on the respective arms, and possibly the connection nipple for attachment of a suction hose, the dissector hereof is electrically insulated by an insulating coating, preferably of friction-resistant synthetic resin material such as polytetrafluroethylene (also known as PTFE or by the trademark TEFLON). At the proximate ends of the arms, a connector plug is provided which includes two prongs which connect the arms to a bipolar electrical power unit.

The dissector hereof thus uniquely permits a surgeon to dissect the tonsillar tissue with the blade on the second arm, remove excess fluid by suction drawn through the opening on the first arm, and then cauterizes the severed blood vessels against hemorrhage by clasping the tissue therebetween, the tissue providing the resistance necessary for electrocauterization. By using the different aspects of the same instrument, the surgery can proceed more efficiently without the time wasted in substituting instruments repeatedly during the surgical procedure.

BRIEF DESCRIPTION OF THE DRAWINGS

FIG. 1 is a right side elevational view of the bipolar suction tonsillar dissector of the present invention showing the tubular suction channel and the opening;

FIG. 2 is a top plan view thereof;

FIG. 3 is a left side elevational view thereof showing the dissecting blade;

FIG. 4 is a bottom view thereof;

FIG. 5 is a fragmentary vertical cross-sectional view taken along line 5—5 of FIG. 4 showing the tubular suction channel extending between the opening on the first arm and the suction connector; and FIG. 6 is an enlarged, fragmentary top plan view of the dissecting blade on the second arm.

DESCRIPTION OF THE PREFERRED EMBODIMENT

Referring now to the drawing, a bipolar suction tonsillar dissector 10 in accordance with the present invention broadly includes a first arm 12, a second arm 14, and a coupling plug 16 for holding the first arm 12 and second arm 14 in substantially parallel, forceps-like relationship. The first arm 12 includes a suction tube 18 defining a suction channel 20 which fluidically communicates between an opening 22 and a suction connector 24. The second arm includes a dissecting blade 26 oriented away from the coupling plug 16.

In greater detail, first arm 12 includes a proximate end 28 and a remote end 30, while second arm 14 includes a corresponding proximate end 32 and a remote end 34. Each arm 12 and 14 is preferably of an electrically conductive material of suitable corrosion-resistance and hardness such as stainless steel as will enable use as a cutting and electrocoagulating tool, but will permit a sufficient degree of resiliency to be used in a forceps-like manner. Thus, the arms 12 and 14 are biased to a normally separated position. The coupling plug 16 is of electrically insulative material such as synthetic resin, with the proximate ends 28 and 32 of the respective arms embedded therein and separated a sufficient distance to prevent the passage of current therebetween.

The coupling plug also includes a pair of electrical prongs 34 and 36 electrically connected to the respective proximate ends 28 and 32 by respective wires within the coupling plug 16. The prongs 34 and 36 are of copper and conventionally spaced for use with electrocoagulating equipment known to those skilled in the art.

As may be seen in FIGS. 1 and 3, the arms 12 and 14 each include a graspable leg 38 including an outboard ridged surface 40, a down bend 42, a connecting stretch 44, a return bend 46, and a shank portion 48. This orientation presents the optimum clearance for the surgeon in using the dissector 10 around obstructions in the patient's mouth or throat.

The arm 12 includes the suction tube 18 which is connected to the respective shank 48 by brazing, welding or the like. The distal portion of the suction tube 18 adjacent the opening 22 presents a tine 50 for use as a suction coagulator, and which may include a small electrode 52 to define a specific location through which current may pass to the tissue and to reinforce the suction tube 18 against current-induced damage. That portion of arm 12 proximal to the tine 50 (excepting the suction connector 24) is provided with a coating 54 of friction-resistant, electrically insulative synthetic resin material, such as PTFE or Teflon. Similarly, the blade 26 presents an opposing tine 56 on arm 14, with that portion of the arm 14 proximal to the tine 56 also provided with coating 54.

Both tine 50 and tine 56 are obtusely angled relative to that portion of the shank 48 adjacent thereto. Most preferably, the tines 50 and 56 are at the same obtuse angle, approximately 120° from the respective shank 48. The blade 26 presents a sharpened, serrated edge 58, best seen in FIG. 6, for facilitating surgical dissection. Most preferably, the tines are approximately 0.5 inches in length.

The opening 22 is oriented distally and cut through the tube 18 on a bias as shown in FIGS. 4 and 5. The orientation of the opening 22, and its size (most preferably a number 7 suction opening) permits fluids such as water, blood, saliva or mucosa to be drawn therethrough and removed from the surgical site.

In use, the surgeon prepares the tonsils as is conventional, and uses the blade 26 and bipolar coagulator to make a mucosal incision. As the tonsil is separated from the anterior pillar, severed blood vessels will cause bleeding at the tonsillectomy site. The surgeon may use the dissector hereof, without changing instruments, to first suction away the fluid and then perform bipolar cauterization of the bleeding site. This greatly limits the tissue damage or scarring to a precise location, and allows the surgeon to continue without substituting or substantially reorienting the instrument. The surgery continues in this manner until all the tonsilar tissue is removed and the hemorrhaging has been stopped. The dissector 10 is then cleaned and autoclaved for the next procedure.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of their invention as pertains to any apparatus not materially departing from but outside the liberal scope of the invention as set out in the following claims.

We claim:

1. Apparatus for surgically dissecting tissue comprising:
   a first elongated arm presenting a proximate end and a remote end, said remote end of said first arm including structure defining an opening proximate thereto, said first arm including a tubular channel for the passage of fluid therethrough connected to and extending from said opening to a suction connector;
   a second elongated arm presenting a proximate end and a remote end, said remote end of said second arm presenting a sharpened dissecting blade;
   means for coupling said proximate end of said first arm proximate to but not in direct contact with said proximate end of said second arm in substantially parallel orientation, for permitting limited movement of said first and second arms toward and away from one another, and for electrically insulating the first arm from the second arm; and
   means for providing electrical bipolar current to said remote ends, whereby tissue held between said blade and said opening defining structure may be cauterized.

2. Apparatus as set forth in claim 1, wherein said current providing means is electrically coupled adjacent the respective proximate ends of said first and second arm, and wherein said first arm and second arm include electrically conductive material.

3. Apparatus as set forth in claim 2, including an electrically insulating coating on a portion of said first and second arms proximate to said respective remote ends.

4. Apparatus as set forth in claim 3, wherein said insulating coating is a friction-resistant synthetic resin material.

5. Apparatus as set forth in claim 1, wherein said current providing means includes first and second electrical terminals respectively connected to said first and second arms.

6. Apparatus as set forth in claim 5, including an electrically insulating coating on a portion of said first and second arms proximate to said remote ends of said first and second arms.

7. Apparatus as set forth in claim 6, wherein said insulating coating is a friction-resistant synthetic resin material.

8. Apparatus as set forth in claim 1, wherein said second arm presents a substantially straight shank and said sharpened dissecting blade is obliquely angled relative to said shank.

9. Apparatus as set forth in claim 8, wherein said sharpened dissecting blade is oriented at an obtuse angle relative to said shank.

10. Apparatus as set forth in claim 1, wherein said dissecting blade presents a serrated edge.

11. Apparatus as set forth in claim 1, wherein said remote end of said first arm includes an electrical contact in facing orientation to said blade, said opening-defining structure orienting said opening substantially away from said blade.

12. Apparatus as set forth in claim 1, wherein said suction connector includes a nipple adapted to receive flexible tubing thereon.

13. A bipolar suction tonsillar dissector comprising:

first and second elongated arms each presenting a respective proximate end and remote end, and including first and second electrocoagulation electrodes at respective remote ends thereof;

a coupling plug for electrically insulating said first arm from said second arm and including a first prong electrically connected to said first arm and a second prong electrically connected to said second arm, said coupling plug normally biasing said first and second arms into a substantially parallel orientation;

an electrically insulating coating covering a portion of said first and second arms proximate to said respective remote ends; and a fluid-carrying channel associated with said first arm including a fluid connector for connecting to a source of suction and an opening adjacent the remote end of the first arm, said second arm including a shank and presenting blade at the remote end thereof presenting a sharpened dissecting edge, said blade being obliquely oriented relative to said shaft.

* * * * *

UNITED STATES PATENT AND TRADEMARK OFFICE
CERTIFICATE OF CORRECTION

PATENT NO. : 5,603,712

DATED : February 18, 1997

INVENTOR(S) : KORANDA, Frank C.

It is certified that error appears in the above-identified patent and that said Letters Patent is hereby corrected as shown below:

On title page, item [54] and col. 1, line 1,
   Title; the first word should be --BIPOLAR-- instead of "BIPOLA".

Signed and Sealed this

Twentieth Day of May, 1997

Attest:

BRUCE LEHMAN

Attesting Officer        Commissioner of Patents and Trademarks